(12) United States Patent
Smith et al.

(10) Patent No.: US 10,791,999 B2
(45) Date of Patent: Oct. 6, 2020

(54) INTERFACE FOR GANTRY AND COMPONENT

(71) Applicant: General Electric Company, Schenectady, NY (US)

(72) Inventors: Brandon Smith, Waukesha, WI (US); Edward Emaci, Brookfield, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 532 days.

(21) Appl. No.: 15/153,989

(22) Filed: May 13, 2016

(65) Prior Publication Data
US 2016/0249871 A1 Sep. 1, 2016

Related U.S. Application Data

(63) Continuation-in-part of application No. 14/930,275, filed on Nov. 2, 2015, now Pat. No. 10,219,760.
(Continued)

(51) Int. Cl.
*A61B 6/00* (2006.01)
*A61B 6/03* (2006.01)
(Continued)

(52) U.S. Cl.
CPC .............. *A61B 6/035* (2013.01); *A61B 6/032* (2013.01); *A61B 6/107* (2013.01); *A61B 6/40* (2013.01); *A61B 6/42* (2013.01); *A61B 6/4208* (2013.01); *A61B 6/4225* (2013.01); *A61B 6/4233* (2013.01); *A61B 6/44* (2013.01); *A61B 6/4411* (2013.01); *A61B 6/4429* (2013.01); *A61B 6/4435* (2013.01); *A61B 6/4441* (2013.01); *A61B 6/4447* (2013.01); *H01J 35/16* (2013.01);
(Continued)

(58) Field of Classification Search
CPC ........ A61B 6/032; A61B 6/035; A61B 6/0407; A61B 6/107; A61B 6/4225; A61B 6/4233; A61B 6/44; A61B 6/4429; A61B 6/4435; A61B 6/46; A61B 6/464; A61B 6/40; A61B 6/4441; A61B 6/4447; A61B 6/42; A61B 6/4208; A61B 6/4411; H01J 35/16; H05G 1/02; H05G 1/04
USPC .... 378/4, 19, 189, 196, 197, 15; 250/370.09
See application file for complete search history.

(56) References Cited

U.S. PATENT DOCUMENTS 4,893,321 A * 1/1990 Eitner .................... A61B 6/145
378/119
4,905,268 A * 2/1990 Mattson ................. A61B 6/032
378/150
(Continued)

OTHER PUBLICATIONS

Authors et. al.: Disclosed Anonymously, "Nested Shielding for Blocking Scattered Xrays", An IP.com prior Art Database Technical Disclosure, IP.com No. IPCOM000199836D, IP.com Electronic Publication Date: Sep. 17, 2010; 6 pages.

*Primary Examiner* — Allen C. Ho
(74) *Attorney, Agent, or Firm* — McCoy Russell LLP

(57) ABSTRACT

A support structure and an imaging component are provided in an imaging system. The imaging component comprises a port extension that frames an opening for x-ray emission. The support structure comprises a recess for receiving the port extension, the recess also framing an opening for x-ray transmission. The imaging system may be a computed tomography (CT) imaging system, x-ray diagnostic system, or other imaging system.

20 Claims, 11 Drawing Sheets

Related U.S. Application Data which is a continuation of application No. 14/171,892, filed on Feb. 4, 2014, now Pat. No. 9,204,850.

(51) Int. Cl.
| | |
|---|---|
| *A61B 6/10* | (2006.01) |
| *H01J 35/16* | (2006.01) |
| *H05G 1/02* | (2006.01) |
| *H05G 1/04* | (2006.01) |
| *A61B 6/04* | (2006.01) |

(52) U.S. Cl.
CPC ............... *H05G 1/02* (2013.01); *H05G 1/04* (2013.01); *A61B 6/0407* (2013.01)

(56) References Cited

U.S. PATENT DOCUMENTS

| | | | | |
|---|---|---|---|---|
| 5,479,021 A * | 12/1995 | Morgan | ............. | A61B 6/032 250/363.04 |
| 5,487,098 A * | 1/1996 | Dobbs | ............. | A61B 6/032 378/19 |
| 5,636,259 A * | 6/1997 | Khutoryansky | ......... | A61B 6/00 378/197 |
| 5,703,921 A * | 12/1997 | Fujita | ............. | A61B 6/035 378/15 |
| 5,834,780 A * | 11/1998 | Morgan | ............. | G01T 1/1615 250/363.04 |
| 5,991,357 A * | 11/1999 | Marcovici | ............. | A61B 6/035 250/370.09 |
| 6,060,712 A * | 5/2000 | Morgan | ............. | G01T 1/1615 250/363.04 |
| 6,314,157 B1 * | 11/2001 | Tachizaki | ............. | A61B 6/035 378/19 |
| 6,519,312 B1 * | 2/2003 | Tybinkowski | ......... | A61B 6/035 378/15 |
| 6,587,538 B2 | 7/2003 | Igarashi | ............. | A61B 6/06 250/367 |
| 6,590,953 B2 * | 7/2003 | Suzuki | ............. | A61B 6/035 310/211 |
| 6,810,103 B1 * | 10/2004 | Tybinkowski | ......... | A61B 6/032 250/363.04 |
| 6,890,100 B2 * | 5/2005 | Reznicek | ............. | A61B 6/035 378/15 |
| 6,917,664 B2 * | 7/2005 | Chappo | ............. | A61B 6/032 378/15 |
| 7,015,476 B2 * | 3/2006 | Juni | ............. | G01T 1/1642 250/363.01 |
| 7,029,176 B2 * | 4/2006 | Martti | ............. | A61B 6/145 378/197 |
| 7,076,018 B2 * | 7/2006 | Russinger | ............. | A61B 6/035 378/15 |
| 7,105,825 B2 * | 9/2006 | Juni | ............. | G01T 1/1644 250/363.04 |
| 7,108,421 B2 * | 9/2006 | Gregerson | ............. | A61B 6/4405 378/197 |
| 7,190,759 B2 * | 3/2007 | Ratzmann | ............. | A61B 6/035 250/370.09 |
| 7,235,788 B2 * | 6/2007 | Von der Haar | ......... | A61B 6/032 250/363.05 |
| 7,257,195 B2 * | 8/2007 | Freund | ............. | G21K 1/025 378/147 |
| 7,281,848 B2 * | 10/2007 | Kendall | ............. | A61B 6/035 378/193 |
| 7,290,929 B2 * | 11/2007 | Smith | ............. | H05G 1/02 378/121 |
| 7,396,160 B2 * | 7/2008 | Tybinkowski | ......... | A61B 6/032 378/147 |
| 7,465,931 B2 * | 12/2008 | Vogtmeier | ............. | A61B 6/4233 250/370.09 |
| 7,489,516 B2 * | 2/2009 | Lacey | ............. | A61B 6/032 250/370.08 |
| 7,519,157 B2 * | 4/2009 | Hockersmith | ......... | A61B 6/4429 378/121 |
| 7,525,097 B2 * | 4/2009 | Dorscheid | ............. | G01T 1/2018 250/370.09 |
| 7,564,940 B2 * | 7/2009 | Mattson | ............. | A61B 6/032 250/370.09 |
| 7,606,346 B2 * | 10/2009 | Tkaczyk | ............. | A61B 6/032 250/370.09 |
| 7,783,000 B2 * | 8/2010 | Kotooka | ............. | A61B 6/032 250/370.09 |
| 7,927,013 B2 * | 4/2011 | Luecke | ............. | A61B 6/035 250/363.05 |
| 7,942,576 B2 * | 5/2011 | Zhao | ............. | H05G 1/02 250/496.1 |
| 8,290,119 B2 * | 10/2012 | Tancredi | ............. | A61B 6/14 378/197 |
| 8,306,182 B2 * | 11/2012 | Yaoi | ............. | A61B 6/035 250/370.09 |
| 8,462,911 B2 * | 6/2013 | Vesel | ............. | A61B 6/032 378/210 |
| 8,483,352 B2 * | 7/2013 | Hoffman | ............. | A61B 6/032 378/19 |
| 8,483,362 B2 * | 7/2013 | Freund | ............. | G21K 1/025 378/147 |
| 8,488,736 B2 * | 7/2013 | Hoffman | ............. | A61B 6/032 378/19 |
| 8,681,930 B2 * | 3/2014 | Sharpless | ............. | A61B 6/035 378/197 |
| 8,693,621 B2 * | 4/2014 | Thran | ............. | A61B 6/4021 378/17 |
| 8,768,032 B2 * | 7/2014 | Basu | ............. | G06T 11/005 250/559.05 |
| 8,781,061 B2 * | 7/2014 | Mochitate | ............. | A61B 6/035 378/189 |
| 8,890,079 B2 * | 11/2014 | Kurochi | ............. | G01T 1/16 250/363.1 |
| 8,987,675 B2 * | 3/2015 | Kato | ............. | A61B 6/4429 250/363.1 |
| 9,044,151 B2 * | 6/2015 | Lacey | ............. | A61B 6/03 |
| 9,044,152 B2 * | 6/2015 | Abenaim | ............. | G01N 23/046 |
| 9,125,613 B2 * | 9/2015 | Gregerson | ............. | A61B 6/4488 |
| 9,198,631 B2 * | 12/2015 | Hara | ............. | A61B 6/508 |
| 9,200,948 B2 * | 12/2015 | Jan | ............. | A61B 6/035 |
| 9,204,850 B2 * | 12/2015 | Smith | ............. | A61B 6/10 |
| 9,208,918 B2 * | 12/2015 | Tybinkowski | ......... | G21K 1/02 |
| 9,332,945 B2 * | 5/2016 | Kodaira | ............. | A61B 6/03 |
| 9,414,793 B2 * | 8/2016 | Kodaira | ............. | E04B 1/82 |
| 9,480,440 B2 * | 11/2016 | Fasoli | ............. | G01N 23/04 |
| 9,526,461 B2 * | 12/2016 | Gregerson | ............. | A61B 6/032 |
| 9,668,330 B2 * | 5/2017 | Matsuzawa | ............. | A61B 6/035 |
| 9,737,273 B2 * | 8/2017 | Gregerson | ............. | A61B 6/035 |
| 9,820,707 B2 * | 11/2017 | Atzinger | ............. | A61B 6/4441 |
| 9,848,837 B2 * | 12/2017 | Sheridan | ............. | A61B 6/035 |
| 9,888,886 B2 * | 2/2018 | Distler | ............. | A61B 6/035 |
| 9,924,915 B2 * | 3/2018 | Kodaira | ............. | F24F 7/065 |
| 10,022,095 B2 * | 7/2018 | Bichler | ............. | A61B 6/0407 |
| 10,219,760 B2 * | 3/2019 | Smith | ............. | A61B 6/10 |

* cited by examiner

INTERFACE FOR GANTRY AND COMPONENT

PRIORITY AND REFERENCE TO RELATED APPLICATIONS

This application is a continuation-in-part of U.S. patent application Ser. No. 14/930,275, entitled "ROTARY MEMBER WITH SAFETY MECHANISM", filed Nov. 2, 2015, which is a continuation of U.S. patent application Ser. No. 14/171,892, entitled "GANTRY WITH SECONDARY SAFETY MECHANISM", filed Feb. 4, 2014 and patented on Dec. 8, 2015 as U.S. Pat. No. 9,204,850, the disclosures of which is incorporated by reference herein as if set forth in their entirety.

BACKGROUND

The subject matter disclosed herein relates generally to interface design and, more particularly, interfaces between emission components and related support structures. One example of an emission component is an x-ray tube that emits x-rays. One example of a support structure is a rotary member of a computed tomography system. Another example of a support structure is a stationary member of a diagnostic x-ray system.

Gantries, i.e. support structures, are an important part of radiography and tomography systems. A medical imaging system can include a gantry comprising a stationary frame for supporting a rotary member about a scanning axis of the scanner. The rotary member includes a central opening large enough to receive a patient extending along the scanning axis. The rotary member is rotated about a patient during a scanning or imaging procedure. An x-ray tube can be positioned on the rotary member diametrically across the central opening from an array of x-ray detectors. As the rotary member rotates, the x-ray tube projects a beam of energy, or x-rays, along a scan plane, through a patient, and to the detector array. By rotating the x-ray source about the scanning axis and relative to the patient, x-rays are projected through a patient from many different directions. An image of the scanned portion of a patient can be constructed from data provided by the detector array using a computer.

X-ray detectors, x-ray tubes, and other components can be attached to the rotary member of a computed tomography system, a pre-patient collimator of a computed tomography system, the stationary support of an x-ray system, and other systems needing such components. There is a need for systems, devices, and methods to attach such components in ways that do not damage any part of the system, especially the interface where the x-rays emit from the x-ray tube and through the supporting structure.

Further, it is important to reduce unwanted x-ray emission as much as possible. One area to help reduce unwanted x-ray emission is in the interface between the x-ray tube and supporting structure. One type of unwanted x-ray emission is scatter radiation. Scatter radiation emits at an angle that is not helpful for diagnostic imaging and may cause added dose to be received by a patient. Reducing such scatter radiation and other forms of unwanted radiation by improved systems, devices, and methods are proposed.

BRIEF DESCRIPTION

In accordance with an embodiment, a gantry is provided that includes a support structure, comprising: an attachment mechanism to allow imaging components to be attached thereto; and a recess to receive a protruding portion of an attached imaging component; wherein the recess frames an opening for unattenuated transmission of imaging beans through the support structure from the imaging component and provides shielding around the inside edge of the frame to attenuate x-ray transmission through the edge of the frame; and an imaging component attached to the support structure and that emits x-rays; the imaging component comprising a port extension that: (a) protrudes outwards from the side of the imaging component where the imaging component attaches to the support structure; (b) frames an opening from the imaging component to allow unattenuated x-rays to emit from the imaging component towards the support structure; and (c) provides shielding around the edge of the frame to attenuate x-ray transmission through the edge of the frame.

In addition in certain embodiments, the port extension can protrude into the recess such that the frame of the port extension provides a primary shielding effect upon scatter x-ray radiation and the frame of the recess provides a secondary shielding effect upon scatter x-ray radiation. The opening framed by the port extension and the opening framed by the recess can be substantially the same shape and size. The depth of the recess can be larger than the height of the port extension. The width of the recess can be larger than the width of the port extension; and the length of the recess can be larger than the length of the port extension. The support structure can be a stationary structure, rotary member, top cap, or pre-patient collimator. Further, the port extension does not physically contact with the support structure or the recess comprised within the support structure in an embodiment.

In certain embodiments, the gantry is part of a computed tomography system or diagnostic x-ray system. And a detector assembly can be attached to the support structure to receiving x-rays and transmitting detected image data; an image reconstructor to receiving transmitted detected image data and reconstructing images therefrom. The imaging component can be attached to the support structure by a primary attachment mechanism; and the imaging component can be attached to the support structure by a secondary attachment mechanism, the secondary attachment mechanism being a T-slot interface.

Further, in certain embodiments, the gantry includes a button that extends outward from the support structure at a height that is larger than the depth of the recess; a pin extending outward from the imaging component in the same direction as the port extension, wherein the height of the pin is larger than the height of the port extension; and wherein the height of the button and the height of the pin are substantially the same.

In accordance with an embodiment, an x-ray tube apparatus is provided that includes an x-ray tube for emitting x-rays; and a port extension, wherein the port extension: protrudes outwards from the side of the x-ray tube where the x-ray tube apparatus can attach to a support structure; frames an opening from the x-ray tube to allow x-rays to emit from the x-ray tube; and provides shielding around the inside edges of the frame to attenuate x-ray transmission through the edge of the frame. The port extension can comprise steel material, lead material, or other attenuating materials. The port extension opening can be oval or rectangular in some embodiments. The support structure can be a stationary structure, rotary member, top cap, or collimator, where the x-ray tube attaches to the support structure via a primary support mechanism and a secondary support mechanism. The x-ray tube apparatus can further include a pin extending outward from the apparatus in the same direction as the port extension, wherein the height of the pin is larger than the height of the port extension.

In accordance with an embodiment, a support structure is provided that includes an attachment mechanism to allow imaging components to be attached thereto; a recess to receive a protruding portion of an attached imaging component; wherein the recess: frames an opening for unattenuated transmission of imaging beans through the support structure; and provides shielding around the inside edge of the frame to attenuate x-ray transmission through the edge of the frame. The support structure can be a stationary structure, rotary member, top cap, or collimator. The support structure can further include a button that extends outward from the support structure at a height that is larger than the depth of the recess.

In accordance with an embodiment, a method is provided for interfacing an x-ray tube with a support structure, that includes sliding an x-ray tube across the surface of a support structure; wherein the x-ray tube comprises a port extension that protrudes outwards from the side of the imaging component where the imaging component attaches to the support structure; and a pin extending outward from the imaging component in the same direction as the port extension, wherein the height of the pin is larger than the height of the port extension; wherein the support structure comprises a button that extends outward from the support structure at a height that is larger than the height of the port extension; wherein the height of the button and the height of the pin are substantially the same; and wherein, during the sliding of the x-ray tube across the surface of the support structure, the pin and button force separation between the x-ray tube and support structure such that the port extension does not come into contact with the support structure.

DETAILED DESCRIPTION

Figure 1:
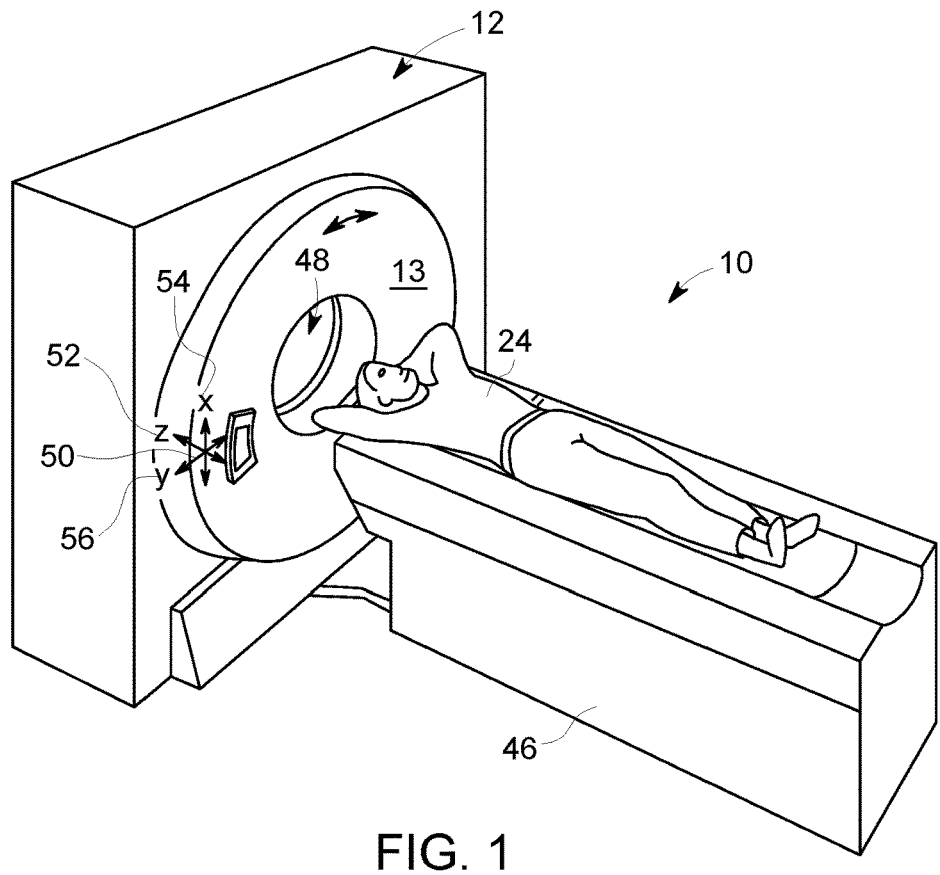
FIG. 1 is an angled view of a medical imaging system with a gantry in accordance with an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 2:
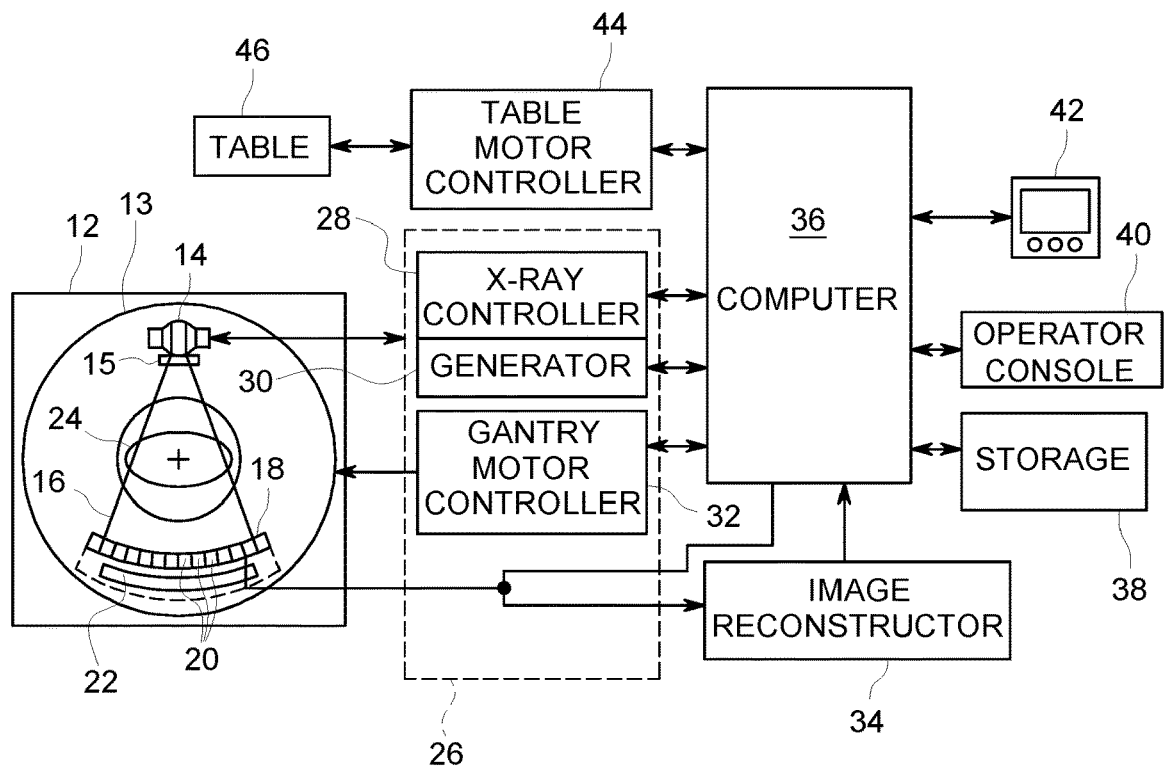
FIG. 2 is a block schematic diagram of a medical imaging system in accordance with an embodiment.

FIGS. 1 and 2 show a computed tomography (CT) imaging system 10 including a gantry 12. Gantry 12 has a rotary member 13. An x-ray source 14 that projects a beam of x-rays 16 through pre-patient collimator 15 toward a detector assembly 18 on the opposite side of the rotary member 13. X-ray source 14 may also be referred to as x-ray tube or x-ray generation component. X-ray source 14 is a type of emissions component. A main bearing may be utilized to attach the rotary member 13 to the stationary structure of the gantry 12. Detector assembly 18 is formed by a plurality of detectors 20 and data acquisition systems (DAS) 22, and can include a post-patient collimator. The plurality of detectors 20 sense the projected x-rays that pass through a subject 24, and DAS 22 converts the data to digital signals for subsequent processing. Each detector 20 produces an analog or digital electrical signal that represents the intensity of an impinging beam of x-rays 16 and hence the attenuated beam as it passes through subject 24. During a scan to acquire x-ray projection data, rotary member 13 and the components mounted thereon can rotate about a center of rotation.

Rotation of rotary member 13 and the operation of x-ray source 14 are governed by a control mechanism 26 of CT imaging system 10. Control mechanism 26 can include an x-ray controller 28 and generator 30 that provides power and timing signals to x-ray source 14 and a gantry motor controller 32 that controls the rotational speed and position of rotary member 13. An image reconstructor 34 receives sampled and digitized x-ray data from DAS 22 and performs high speed image reconstruction. The reconstructed image is output to a computer 36 which stores the image in a computer storage device 38.

Computer 36 also receives commands and scanning parameters from an operator via operator console 40 that has some form of operator interface, such as a keyboard, mouse, touch sensitive controller, voice activated controller, or any other suitable input apparatus. Display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position subject 24 and gantry 12. Particularly, motorized table 46 moves a subject 24 through a gantry opening 48, or bore, in whole or in part. A coordinate system 50 defines a patient or Z-axis 52 along which subject 24 is moved in and out of gantry opening 48, a gantry circumferential or X-axis 54 along which detector assembly 18 passes, and a Y-axis 56 that passes along a direction from a focal spot of x-ray source 14 to detector assembly 18.

Figure 3:
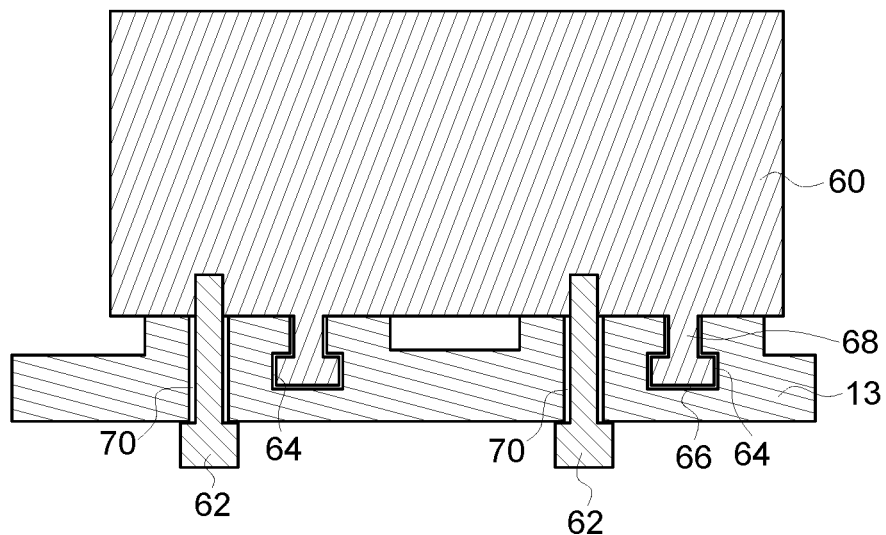
FIG. 3 is a side view of a component attached to a rotary member with primary and secondary attachment mechanisms in accordance with an embodiment.

FIG. 3 shows one view of a rotary member 13 with a component 60 attached thereto, according to one embodiment. Rotary member 13 may also be referred to as a drum or disk. Component 60 can be an x-ray tube, high voltage generator, heat exchanger, collimator, image detector, circuit board chassis, balance weight, power supply, or other item to be attached to rotary member 13.

FIG. 3 shows primary attachment mechanism 62 and secondary attachment mechanism 64 in normal operation conditions. Primary attachment mechanism 62 may be bolts in one embodiment or other types of fastening elements in alternative embodiments. FIG. 3 shows the primary attachment mechanisms 62 attached to component 60 through slots 70. While the primary attachment mechanisms 62 are shown at a perpendicular angle to the rotary member 13, they can be set at alternative angles or orientations for fastening. In normal operation conditions as shown in FIG. 3, primary attachment mechanism 62 is engaged, thus pressed flush against rotary member 13, to prevent any pulling away of component 60 due to centrifugal, gravitational, or other forces during operation of the CT imaging system 10. While FIG. 3 shows the sides of primary attachment mechanism 62 as not flush against rotary member 13 in slot 70, the sides can be flush in alternative embodiments. Slot 70 may have threads to accept bolts or screws in one embodiment. While FIG. 3 shows two primary attachment mechanisms 62, there can be any number in varying embodiments.

Secondary attachment mechanism 64 is shown as a T-slot interface where component 60 has a T-slot fastener 68 that may be slid into T-slot socket 66. T-slot fastener 68 includes a stem and a head. T-slot socket 66 is integrated into the rotary member 13 in this embodiment. In an alternative embodiment, T-slot socket 66 may be attached to rotary member 13. T-slot fastener 68 is integrated into component 60 in this embodiment. In an alternative embodiment, T-slot fastener 68 may be attached to component 60. Secondary attachment mechanism 64 is a safety device in one embodiment. In normal operation conditions shown in FIG. 3, the secondary attachment mechanism 64 is not engaged and is bearing no component load, or weight. Thus, FIG. 3 shows no part of T-slot fastener 68 pressed flush against rotary member 13. Not bearing load during normal operation keeps it as strong as possible and reduces wear. While FIG. 3 shows two secondary attachment mechanisms 64, there can be any number in varying embodiments.

A T-slot interface can be described in one embodiment as a socket having a base defining a recess bordered by a lip, and a fastener having an elongate stem portion and a head slidably insertable into the recess of the socket where it is retained by the lip of the socket.

Figure 4:
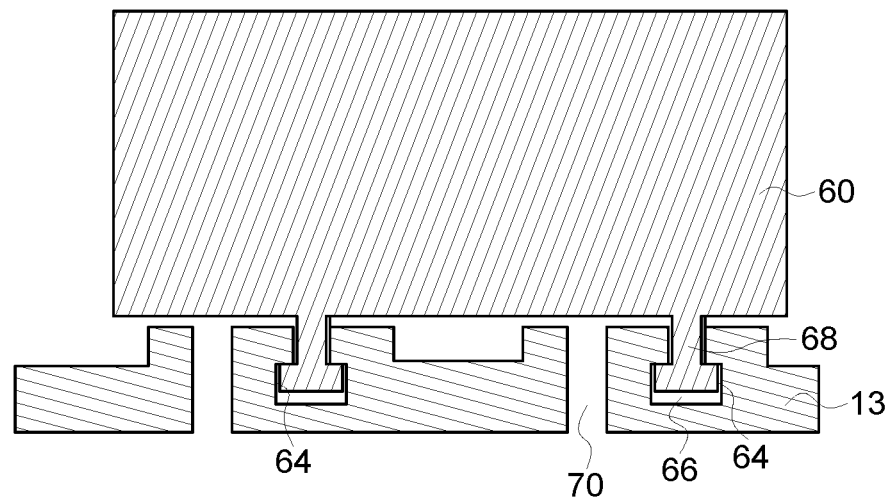
FIG. 4 is a side view of a component attached to a rotary member with a secondary attachment mechanism in accordance with an embodiment.

FIG. 4 shows a system where primary attachment mechanisms 62 are not installed and secondary attachment mechanisms 64 are engaged. Slots 70 in rotary member 13 are empty in this example. This could be in a situation where the primary attachment mechanisms 62 were never put into place, fell out, were not torqued enough for secure fastening, were not the right type of mechanism (wrong length, strength, etc.), are fatigued, are broken, or have had some other issue happen to them. This can be considered a failure condition of a primary attachment mechanism 62. In this situation the secondary attachment mechanism 64 takes the load. This is shown by the head of T-slot fastener 68 being flush against the top part of T-slot socket 66 during rotation as the force pulls component 60 away from rotary member 13. Thus, the secondary attachment mechanisms 64 protect component 60 from being ejected radially or otherwise from the rotary member 13. There also could be a situation where secondary attachment mechanism 64 only takes part of the load, such as when only some of the primary attachment mechanisms 62 are engaged or the primary attachment mechanisms 62 used are weak for some reason.

According to one embodiment, the gaps within the secondary attachment mechanism's T-slot interface allow for audible noise to be made when the secondary attachment mechanism 64 is engaged. This can alert a nearby human operator to notice that the gantry 12 is running in safety, or failsafe, mode and not in normal mode so the operator can attend to the safety issue. The system can be arranged so that the audible noises are only during gantry 12 spin-up and spin-down or all the time during operation. According to an alternative embodiment, the gaps are such that no audible noise can be heard.

The automatic engaging of the secondary attachment mechanism 64 is a failsafe. This can be desirable since a field engineer may not activate the failsafe if it is manual. A manual installed failsafe is subject to incorrect installation itself. According to some embodiments, the system can automatically engage and requires no manual intervention to activate the failsafe protection. Once the component 60 is in place, it will not be thrown from the rotating structure even without any primary attachment mechanisms 62 installed.

Figure 5:
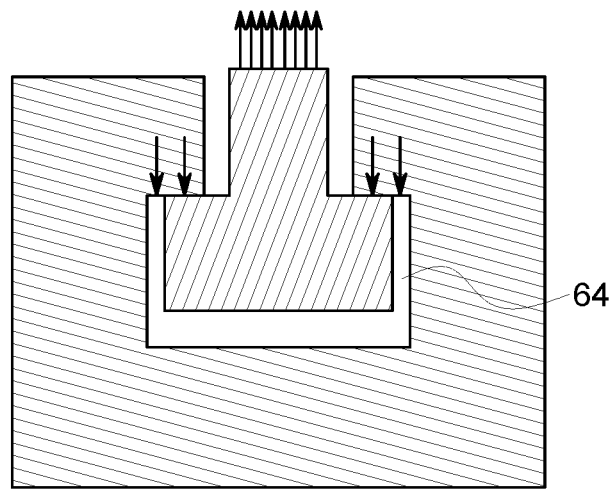
FIG. 5 is a side view of an engaged secondary attachment mechanism in accordance with an embodiment.

FIG. 5 shows an engaged secondary attachment mechanism 64. The design of the secondary attachment mechanism 64 results in substantially even force distribution since load is being carried by both sides of the T-shape according to one embodiment. This increases strength and reliability for the secondary attachment mechanism.

Figure 6:
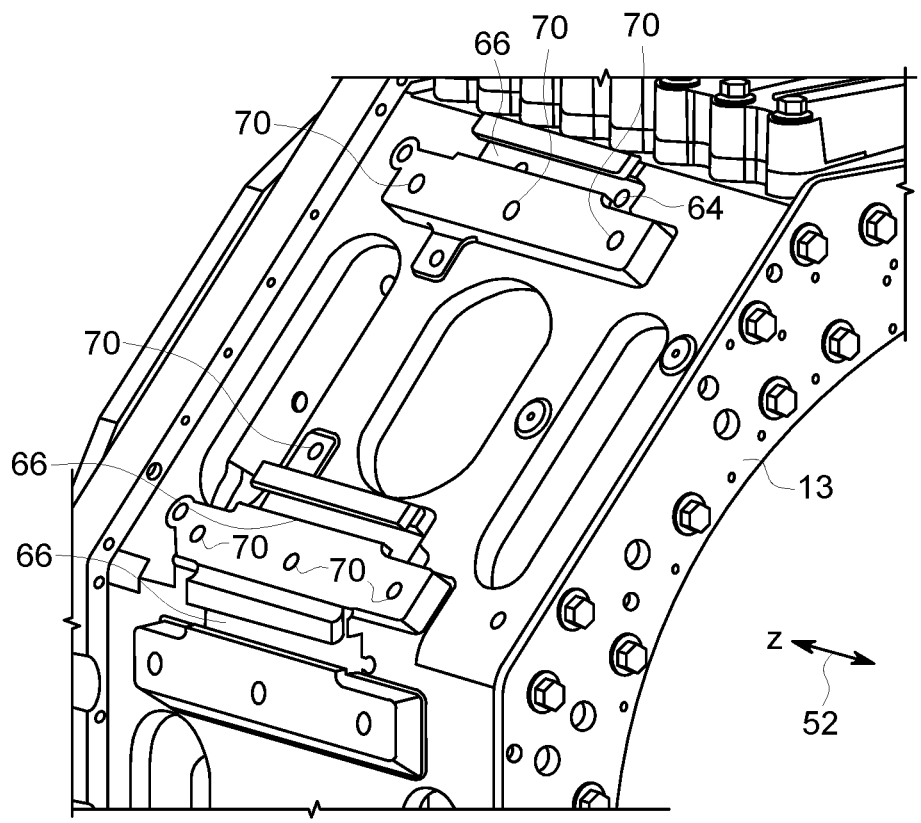
FIG. 6 is an angled view of a rotary member with a t-slot socket in accordance with an embodiment.

FIG. 6 shows an angular view of rotary member 13 that includes one part of the secondary attachment mechanism 64, the T-slot socket 66. A component 60 is first slid in the Z-direction 52 into the rotary member 13. Then primary attachment mechanisms 62 can be installed through slots 70. The slot 70 arrangement shown in FIG. 6 is exemplary. There can be one or more slots 70 and set in various arrangements in rotary member 13.

Figure 7:
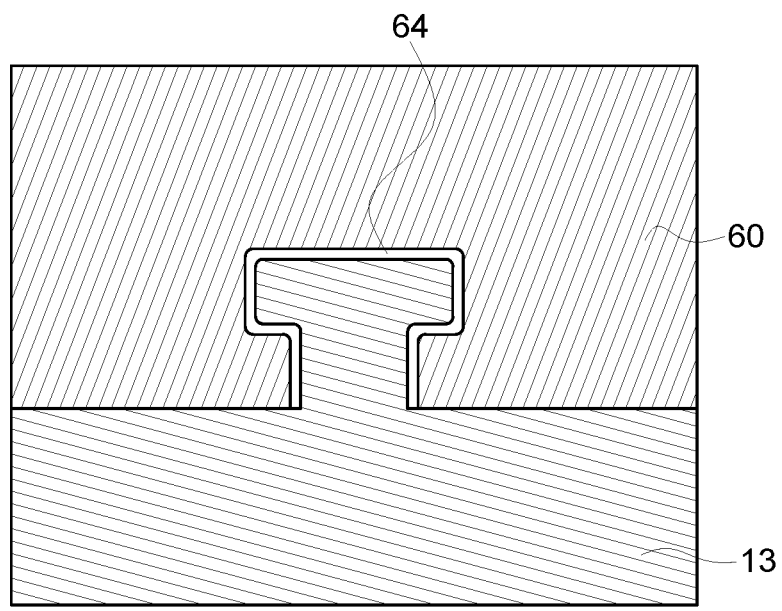
FIG. 7 is a side view of a component attached to a rotary member in accordance with an embodiment.

FIG. 7 shows a view of secondary attachment mechanism 64 in an alternative embodiment. The T-slot fastener is integrated, or attached to, the rotary member 13. The T-slot socket is integrated, or attached to, component 60.

Figure 8:
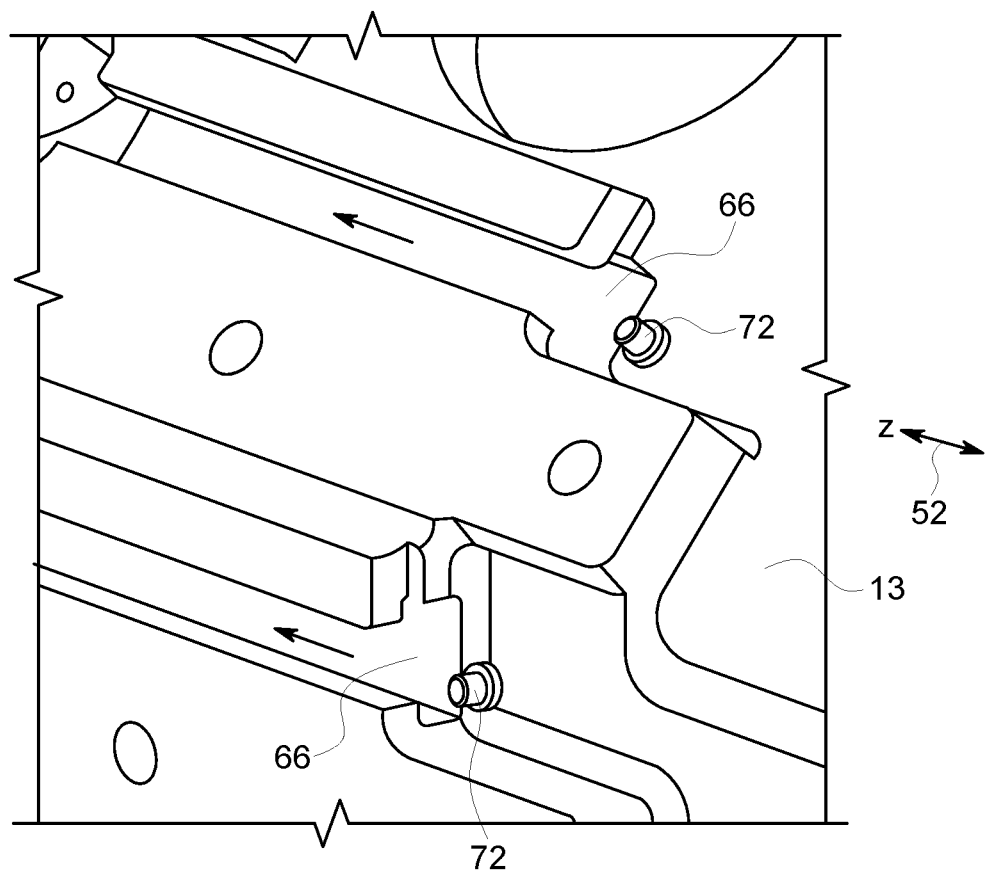
FIG. 8 is an angled view of a rotary member with a t-slot socket and a latch in accordance with an embodiment.
Figure 9:
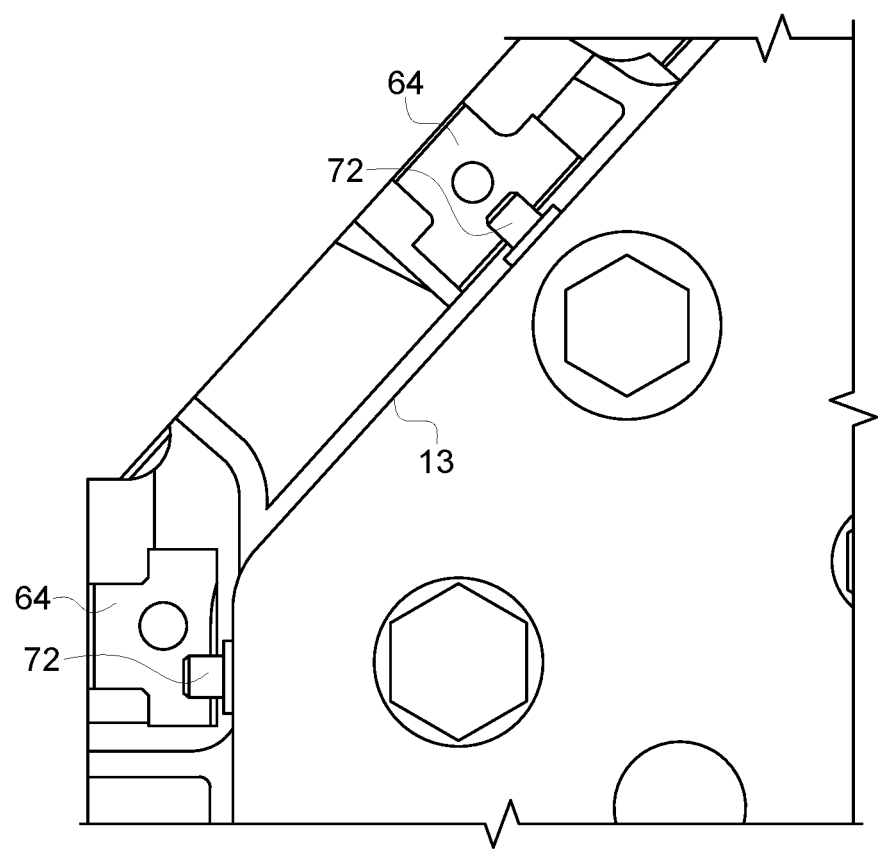
FIG. 9 is a side view of a rotary member with a t-slot socket and a latch in accordance with an embodiment.

FIGS. 8 and 9 show views of rotary member 13 that includes latch 72. Latch 72 depresses as a component slides across it and into T-slot socket 66. FIG. 8 shows an angled view. FIG. 9 shows a front view. A component with T-slot fastener could slide into rotary member 13 in the direction of the arrow shown in the T-slot sockets 66 in FIG. 8. After the component has fully slid into T-slot socket 66, the latch 72 rises to secure the T slot fastener into place in the axial or Z-direction 52. Thus, the latch 72 retains the component in the rotary member 13 T-slot socket 66 in the axial or Z-direction 52. The latch 72 can also be referred to a Z-capture device, spring pin, or other names common to the art. It is a spring pin with a spring mechanism in one example embodiment.

In the design of one embodiment, latch 72 is automatically engaged. It can be disengaged by manual user input or insertion of a component into the gantry's rotary member 13. Latch 72 cannot be left in a disengaged condition in this embodiment. When a user input to the latch 72 is removed or the component is fully inserted, the latch 72 automatically returns to its engaged state. Latch 72 is further held in place when rotational forces push outward in the radial direction.

Figure 10:
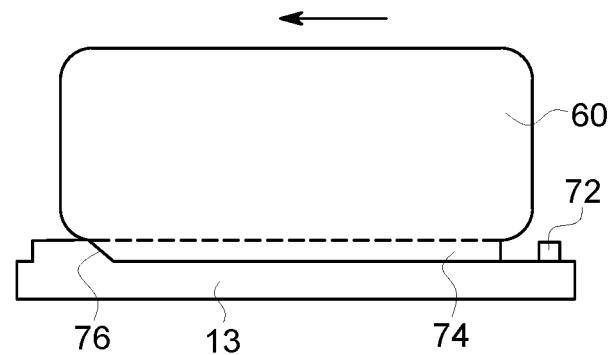
FIG. 10 is a side view of a component inserted into a rotary member in accordance with an embodiment.

FIG. 10 shows a side view of a component 60 inserted into rotary member 13 using the secondary attachment mechanism 64 according to one embodiment. The T-slot fastener head 74 has an angled edge 76 that depresses latch 72 as component 60 is slid into the secondary attachment mechanism 64 of rotary member 13 along the Z-direction 52 of the arrow in FIG. 10. After component 60 is fully inserted, latch 72 automatically rises to block the removal of component 60 without manual input. Angled edge 76 can also be known as a chamfer or ramp.

Figure 11:
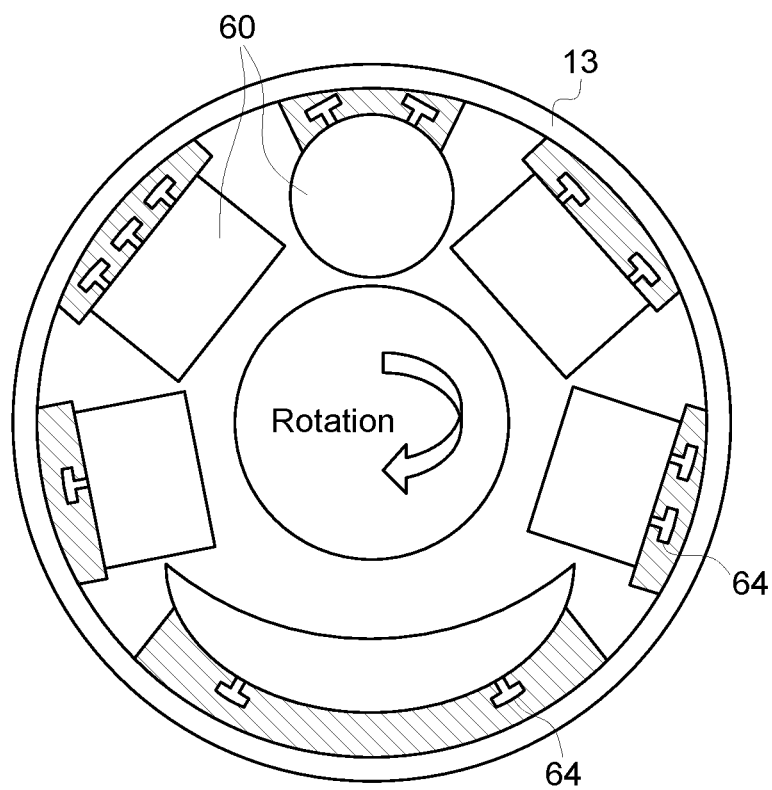
FIG. 11 is a view of components attached to a rotary member in accordance with an embodiment.

FIG. 11 shows additional embodiments of the system. Rotary member 13 has thus far been shown with components 60 on the outside of the rotary member 13. FIG. 11 shows components 60, of various shapes and sizes, attached or mounted to the inside of rotary member 13. Primary attachment mechanisms 62 are still part of the system, but are not shown in the drawing. Secondary attachment mechanisms 64 are shown, sometimes with one, two, or three per component 60 to show the flexibility of the system. In an alternative embodiment, components can be placed on both the inside and outside of rotary member 13.

Both forms of attachment mechanisms help the component 60 stay centered and attached to the respective support structure. The support structure may be a rotary member 13 as discussed above as well as a stationary structure as in a diagnostic x-ray system or baggage scanning system. If the component 60 stays attached and centered, the interfaces between the component 60 and the remaining parts of the system remain aligned and are more likely to function as planned.

Figure 12:
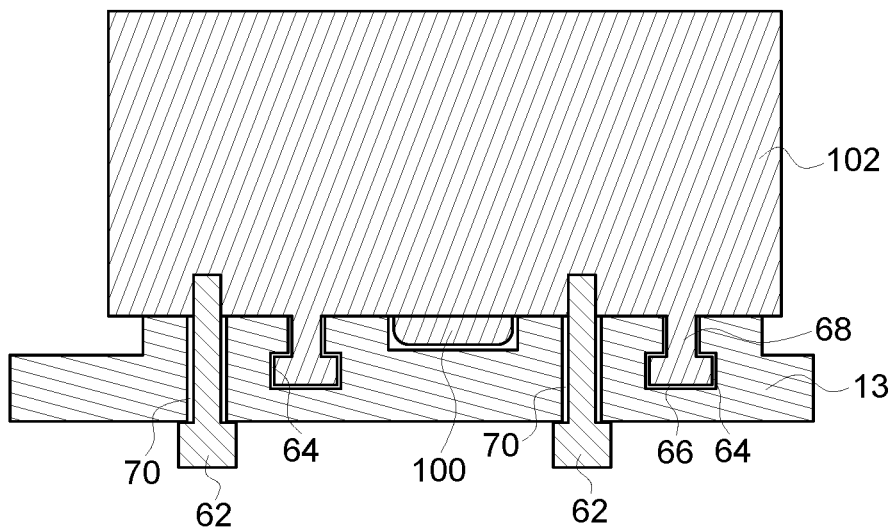
FIG. 12 is a side view of an x-ray generation component attached to a gantry in accordance with an embodiment.

FIG. 12 is a side view of an x-ray generation component attached to a gantry in accordance with an embodiment. FIG. 12 shows component 102 which may be an x-ray tube in an embodiment. Component 102 comprises a port extension 100. Port extension 100 protrudes into a recess in rotary member 13 in the embodiment of FIG. 12, but can extend into a recess of other support structures in alternate embodiments. Thus, FIG. 12 shows an integrated interface. FIG. 12 shows that port extension 100 does not physically contact rotary member 13. FIG. 12 shows that port extension 100 can have rounded edges. In an alternate embodiment, port extension 100 has right angle edges. In an alternate embodiment, port extension 100 has slanted chamfer edges. FIG. 12 shows an overlapping design providing overlapping x-ray shielding against scatter radiation, as is discussed further below.

In this embodiment, the port extension 100 is attached to or within the component 102, and the recess is attached to or within the rotary member 13. In an alternate embodiment, the port extension 100 is attached to or within a support structure and the recess is attached to or within the component 102.

Figure 13:
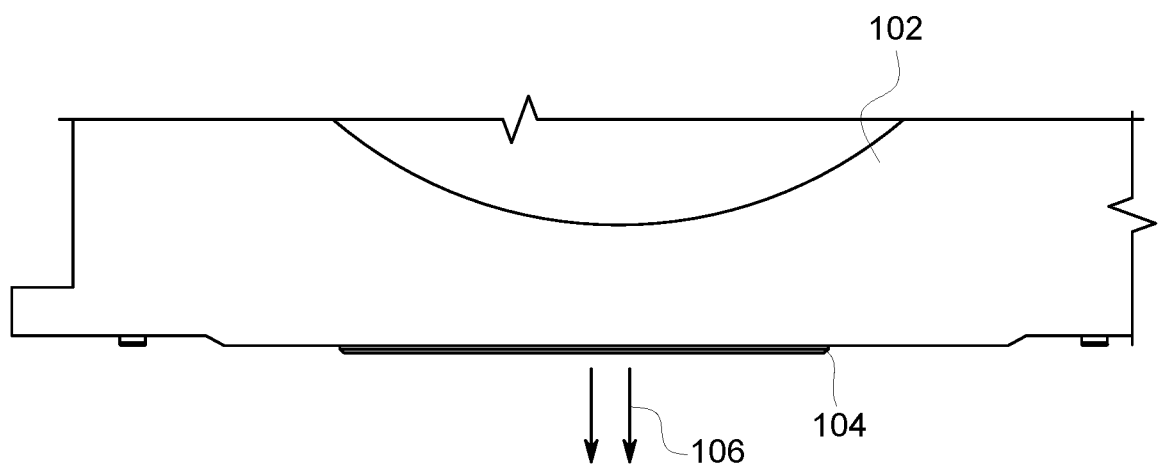
FIG. 13 is a side view of an x-ray generation component with a port extension in accordance with an embodiment.

FIG. 13 is a side view of an x-ray generation component with a port extension 104 in accordance with an embodiment. Component 102 is shown with a port extension 104. Port extension 104 has chamfered edges in the embodiment of FIG. 13. The chamfer rises inward around the end of the port extension 104. Port extension 104 protrudes from the lower surface of component 102 in the direction of the emission of x-rays 106. X-rays 106 are being emitted out of the component 102 which is an x-ray tube. Port extension 104 frames an opening from the x-ray tube component 102 to allow x-rays 106 to emit from the x-ray tube component 102. X-rays 106 may also be referred to as the imaging beam.

Figure 14:
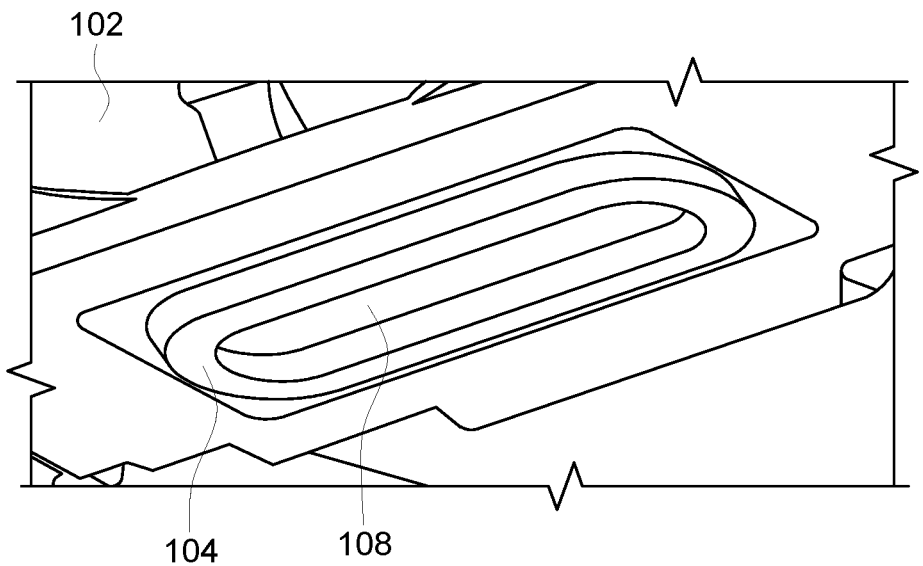
FIG. 14 is a perspective view of a port extension of an x-ray generation component in accordance with an embodiment.

FIG. 14 is a perspective view of a port extension 104 of an x-ray generation component in accordance with an embodiment. Port extension 104 is shown as protruding outwards from the surface of component 102. Port extension 104 frames the port opening 108 that allows unattenuated x-rays to be transmitted from the x-ray generation component 102. Port opening 108 is shown as oval in FIG. 14, but may be other shapes such as a ring, rectangle, octagon, or other shapes as is reasonable for the application.

Figure 15:
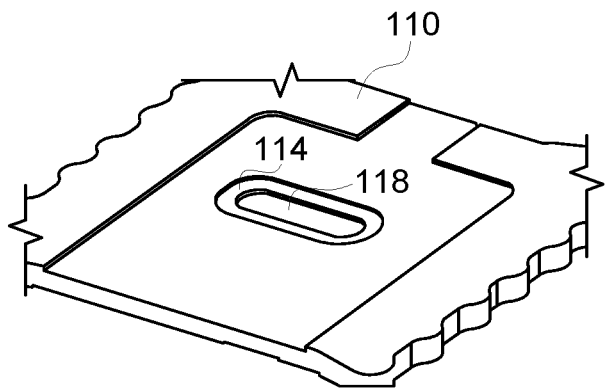
FIG. 15 is a perspective view of a gantry section for receiving an x-ray generation component in accordance with an embodiment.

FIG. 15 is an isometric perspective view of a gantry section for receiving an x-ray generation component in accordance with an embodiment. FIG. 15 shows base 110, recess 114, and base opening 118. Base 110 maybe within or attached to a support structure such as rotary member 13, a pre-patient collimator, or a stationary support structure, such as for medical scanning or baggage scanning. If base 110 is a separate piece attached to such structures in certain embodiments, it may be called a top cap. Base 110 comprises a recess 114, also called a recessed pocket as it can be a machined pocket. Recess 114 surrounds the component port extension. Recess 114 has a shielded edge, shown further in FIG. 16. Recess 114 comprises base opening 118. Base opening 118 allows for the unattenuated, or substantially unattenuated, passage of x-rays or other imaging beams. Base opening 118 is shown as oval in FIG. 15, but may be other shapes such as a ring, rectangle, octagon, or other shapes as is reasonable for the application.

Figure 16:
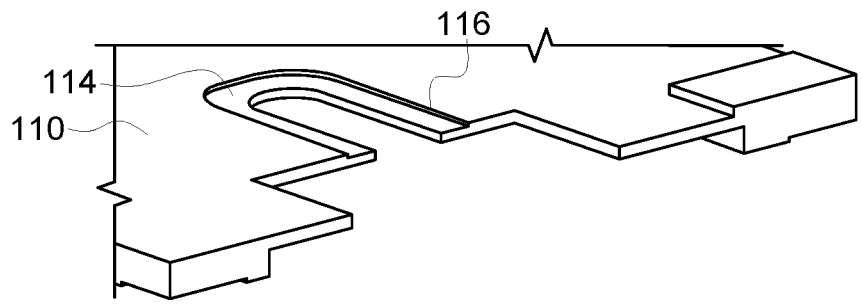
FIG. 16 is a cross section view of a gantry section for receiving an x-ray generation component in accordance with an embodiment.

FIG. 16 is a cross section view of a gantry section for receiving an x-ray generation component in accordance with an embodiment. FIG. 16 is a section view including base 110, recess 114, and shielded recess edge 116. Shielding within the edge blocks the flow of x-ray radiation in the direction of the recess edge 116.

Figure 17:
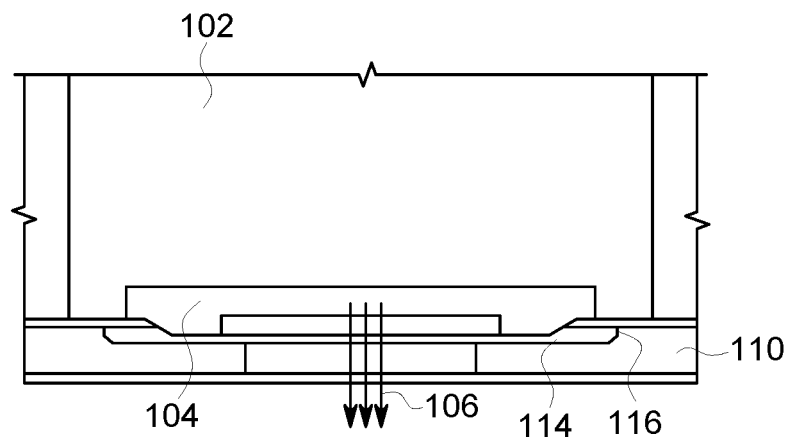
FIG. 17 is a view of an in-use x-ray generation component attached to a gantry in accordance with an embodiment.

FIG. 17 is a view of an in-use x-ray generation component attached to a gantry in accordance with an embodiment. Component 102 comprises a port extension 104 that is either attached to or embedded within component 102. Base 110 comprises a recess 114 for receiving port extension 104. The tube port extension 104 protrudes into recess 114 in the gantry to provide a physically overlapping design to the interface. X-rays 106 emit from x-ray generation component 102, through the opening of port extension 104, and through the opening of base 110 to be transmitted through an object to be imaged.

To prevent scatter radiation, port extension 104 has shielding around the frame of its opening, and recess 114 has a shielded recess edge 116. This double shielding approach can be called an overlapped approach, nested approach, or labyrinth approach. Port extension 104 protrudes into recess 114 such that the frame of port extension 104 provides a primary shielding effect upon scatter x-ray radiation and the frame of the recess provides a secondary shielding effect upon scatter x-ray radiation. The overlapping design ensures that there is no line of sight for scattered x-rays to escape without passing through shielding. Any scattered x-rays that impinge on the gantry tube interface structure, recess walls, or port extension are attenuated. The level of attenuation depends on the material selection, physical overlap, and part thicknesses. In an embodiment, steel is used for port extension 104 and recess 114. Other materials can be used such as lead, injection molded tungsten plastic, or other materials with high x-ray attenuation rates. This approach helps for large coverage tubes. This approach allows for lower dose and the control of unwanted leakage radiation, radiation that is not actually used for imaging. This unwanted radiation could enter the patient, operator, or others in the area that are not supposed to be affected by the radiation. Thus, preventing unwanted radiation is a benefit for health and safety.

Figure 18:
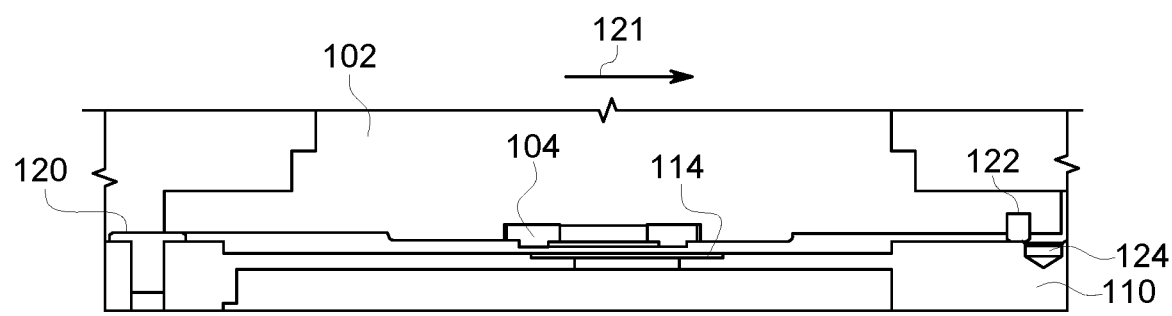
FIG. 18 is a side view of an x-ray generation component being installed in a gantry in accordance with an embodiment.

FIG. 18 is a side view of an x-ray generation component being installed in a gantry in accordance with an embodiment. And FIG. 19 a zoomed view of an x-ray generation component being installed in a gantry in accordance with an embodiment. The x-ray generation component is slidably inserted into the support structured and then it lowers into place once the port extension and recess are aligned, in such a way that contact between the port extension and the support structure is not made. Both FIG. 18 and FIG. 19 will be discussed together as they detail the mid-installation view of the system, interface, apparatus, and method.

Figure 19:
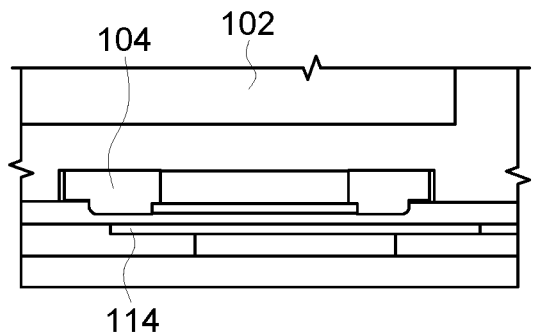
FIG. 19 a zoomed view of an x-ray generation component being installed in a gantry in accordance with an embodiment.

FIGS. 18 and 19 shows x-ray generation component 102 being installed, in the installation direction 121, onto base 110. Component 102 comprises a protruding port extension 104 that is not in contact with base 110 during, or after, installation. This is made possible during installation by base button 120 holding up component 102 as it slides into the base on the left side of FIG. 18. Base button 120 extends outward from the base at a height that is larger than the depth of recess 114. The non-contact is also made possible by component pin 122 that holds the other side of component 102 aloft to prevent contact of the port extension 104 from the base 110 or its recess 114. Component pin 122 extends outward from the component in the same direction as the port extension 104, wherein the height of the pin is larger than the height of the port extension 104, as shown further in FIG. 20. Base button 120 may also be called a gantry button or protruding feature. Component pin 122 may also be called a tube pin, protruding feature, or dowel pin. Base button 120 and Component pin 122 work together to keep component 102 aloft during installation and removal. The slide and lower installation method works well with the secondary attachment mechanism such as a t-slot as mentioned above with reference to FIG. 10, for example.

When port extension 104 is correctly aligned with recess 114, component pin 122 will be correctly aligned with base pin slot 124 and component 102 will have no remaining portion above base button 120. This allows component 102 to lower onto base 110 only when correctly aligned such that port extension 104 does not come in contact with any portion of base 110 or recess 114. When installed, shown further in FIG. 20, port extension 104 is fully within, but not in contact with, recess 114. Component pin 122 is the same, or substantially the same, height as base button 120, as far as the heights they extend outward from the surface of the component and base, respectfully. Note that the button and pin are currently installed on different structures in an embodiment. In alternate embodiments, the button and pin could be on the same structure, either the x-ray component or the support structure.

Because port extension 104 never comes in contact with base 110, port extension 104 can remain error free, avoid misuse, and avoid damage. The installation and removal of component 102 into base 110 does not allow for such contact. The installation or removal can be protected against damage using these physical design features. Thus, the integrity of the shielding seal of the interface is maintained and scatter radiation is kept lower. Further, this prevents part damage or infiltration of foreign material (metal, dust, and etcetera) into the pre-patient collimator or other attached components. Whether the tube is being installed or removed, the field engineer or operator perform the needed operation without these parts coming into contact and becoming damaged with handling.

Further, the potential for imaging artifacts is reduced by this design. Metal particles that find their way into the pre-patient collimator can get into the image chain and cause imaging artifacts. Because of the non-contact radiation shielding, there is no way to generate metal particles from rubbing parts in the vicinity of the gantry recess area. Any parts that rub in this area risk putting metal particles into the pre-patient collimator; the gantry recess area may be open to the pre-patient collimator. The contact between the component and base in other areas (pin 122 and pin slot 124; button 120 and component 102) is sufficiently far from the gantry recess area that particles will not fall into the pre-patient collimator.

Figure 20:
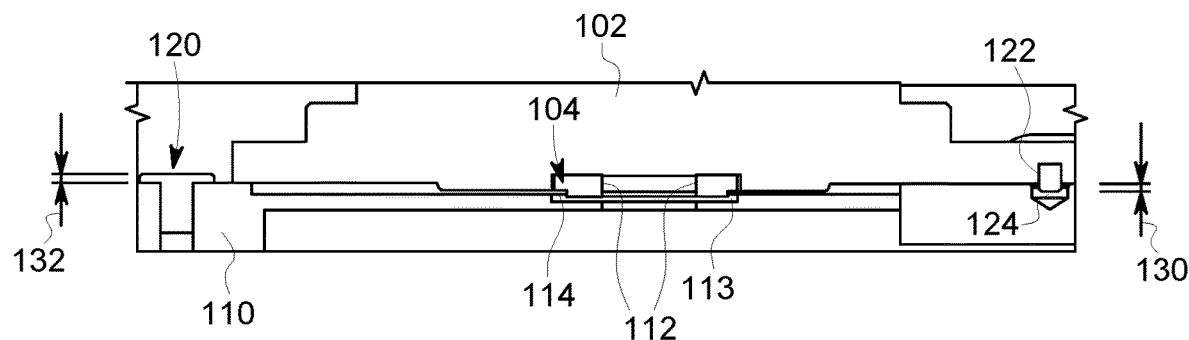
FIG. 20 is a side view of an installed x-ray generation component after installation into a gantry in accordance with an embodiment.

FIG. 20 is a side view of an installed x-ray generation component after installation into a gantry in accordance with an embodiment. Installation is now complete. Component 102 is attached to base 110 through primary and/or secondary attachment mechanisms, as discussed above. None of component 102 is resting on base button 120. Component pin 122 is lowered and within base pin slot 124. Port extension 104 is lowered and within, but not in contact with, recess 114.

When the tube component 102 is installed at the position for normal imaging, port extension 104 protrudes into gantry recess 114. Base button height 132 and component pin protrusion height 130 are both larger than the amount of protrusion of port extension 104. Thus, contact is controlled for the component 102 and prevented for protruding port extension 104.

Port extension shielding 112 around the frame of the port extension opening is a first prevention of scatter x-ray radiation. Recess shielding 113 is a second, overlapping, prevention of scatter x-ray radiation. Dual shielding is thus achieved for scatter radiation. Thus, FIG. 20 shows a self-protecting x-ray tube and gantry interface for integrated x-ray scatter shielding.

Figure 21:
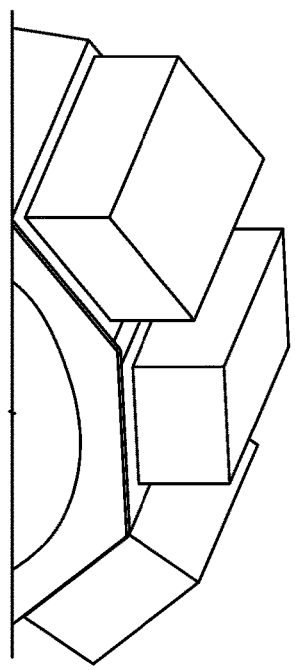
FIG. 21 is a perspective view of an installed x-ray generation component on a rotary member of a CT system gantry in accordance with an embodiment.

FIG. 21 is a perspective view of an installed x-ray generation component on a rotary member of a CT system gantry in accordance with an embodiment. As an alternative, interfaces in varying embodiments may also be applied to other types of radiation generating equipment such as fixed or mobile radiographic systems.

Figure 22:
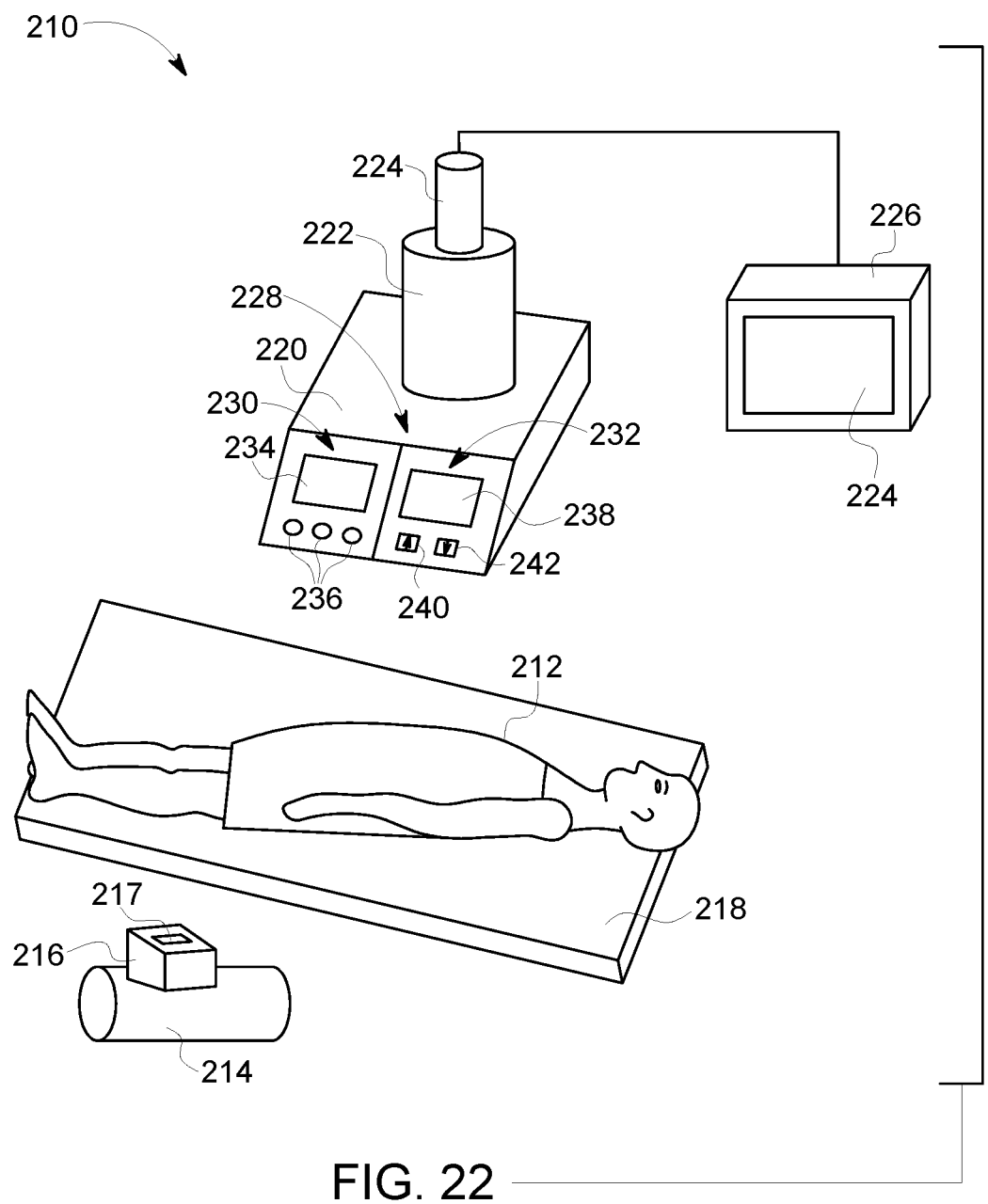
FIG. 22 is a view of an installed x-ray generation component on an X-ray system gantry in accordance with an embodiment.

FIG. 22 is a view of an installed x-ray generation component on an X-ray system gantry in accordance with an embodiment. The port extension and recess interface between x-ray tube and its support structure, such as the pre-patient collimator 216 in this embodiment, can be implemented in such an embodiment.

FIG. 22 illustrates an exemplary diagnostic imaging system 210 configured to continuously image the internal features of a subject, such as anatomy of a human subject or patient 212 in a medical or screening context, throughout an imaging operation. The illustrated diagnostic imaging system 210 includes an X-ray tube 214 with a collimator 216, a port 217, and filters (not shown), a table 218 on which the patient is positioned, an imaging console 220, an image intensifier 222, a camera 224, and a monitor 226. The imaging console 220 includes a user interface 228 including a first control panel 230 and a second control panel 232. The first control panel 230 includes a display 234 and a plurality of configurable adjustments 236. The second control panel 232 includes a display 238 and a plurality of configurable adjustments 240 and 242, which are configured to increase or decrease a parameter value, respectively. The monitor 226 also includes a display 224 configured to display a sequence of images to an operator during the imaging operation.

During operation, the X-ray source 214 generates an X-ray beam, for example, via a conventional cathode and anode X-ray production system. In some embodiments, the X-ray beam may be filtered to provide the desired energy spectrum before reaching the pre-patient collimator 216. To that end, some embodiments may include one or more desired filters such as energy based filters (e.g., aluminum), equalization filters (e.g., trough filters, bow-tie filters, wedge filters, etc.), and so forth. Further, the size and shape of the X-ray beam is adjusted by the pre-patient collimator 216 before emerging from the port 217. After emerging from the port 217, the X-ray beam passes through the table 218 and the patient 212 positioned thereon. The x-ray source 214 may have a port extension, and the pre-patient collimator 216 may have a recess to receive the x-ray source port extension, as discussed further above.

The X-ray beam is attenuated by the patient's anatomy, and at least a portion of the attenuated beam is detected by a high sensitive detector of the image intensifier 222 mounted to the imaging console 220. The image intensifier 222 is adapted to produce a projection image of an acceptable quality from a low number of X-ray photons. Such a feature may be advantageous in fluoroscopy systems since continuous imaging throughout the imaging operation may expose the patient to substantial quantities of X-ray energy. The output signals from the image intensifier 222 are continuously transferred via the video camera 224 to the monitor 226 for viewing on the display 244 during the imaging operation.

It should be noted that, while the present disclosure refers to the use of the x-ray system in a medical diagnostic context, the system may be used in different contexts as well. For example, with human subjects, the system may be used for screening and similar applications. In other environments, the system may be used for detection of items in parcels, luggage, transport vehicles, and so forth. Still further, in some embodiments, such x-ray imaging systems may be utilized for inspection of industrial parts, such as pipes or wind blades.

The system disclosed provides beneficial safety features, maintenance features, image quality improvements, and interface mechanisms. Installers have an easy to implement installation structure. Patients and operators have less dose to worry about. Radiologist have higher quality images with less artifacts. And the hardware itself may last longer and need less maintenance.

Because there is no contact between protruding and recessed features of the critical areas used for radiation shielding, the integrity of the shielding remains intact and consistent. This ensures that the radiation shielding is effective for the life of the product. It also ensures that the next tube that is installed also has effective shielding, gantry-side shielding effectiveness is not affected by tube removal or installation. The system is robust and will not be affected by the number of tube changes.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An x-ray tube apparatus, comprising:
an x-ray tube for emitting x-rays comprising a fastener extending from the x-ray tube;
a primary attachment mechanism;
a secondary attachment mechanism; and
a port extension, wherein the port extension:
protrudes outwards from a side of the x-ray tube, wherein the x-ray tube attaches to a support structure of a gantry at the side via the primary attachment mechanism and the secondary attachment mechanism, wherein the secondary attachment mechanism is located in the support structure of the gantry and engages with the fastener extending from the x-ray tube;
frames an opening from the x-ray tube to allow x-rays to emit from the x-ray tube; and
provides shielding around inside edges of the opening to attenuate x-ray transmission through the inside edges of the opening.

2. The x-ray tube apparatus of claim 1, wherein:
the port extension further comprises steel material.

3. The x-ray tube apparatus of claim 1, wherein:
the x-ray tube attaches to the support structure via the primary attachment mechanism and the secondary attachment mechanism interfacing with corresponding attachment mechanisms of the support structure.

4. The x-ray tube apparatus of claim 3, wherein:
the support structure comprises a stationary structure, a rotary member, a top cap, or a collimator, wherein the primary attachment mechanism and the secondary attachment mechanism are configured to interface with corresponding attachment mechanisms of the stationary structure, the rotary member, the top cap, or the collimator.

5. The x-ray tube apparatus of claim 1, wherein:
the opening is oval or rectangular.

6. The x-ray tube apparatus of claim 1, further comprising:
a pin extending outward from the x-ray tube in a same direction as the port extension, wherein a height of the pin is larger than a height of the port extension.

7. A support structure, comprising:
an attachment mechanism to allow imaging components to be attached thereto,
wherein the attachment mechanism comprises a primary attachment mechanism and a secondary attachment mechanism, and
wherein the primary attachment mechanism and the secondary attachment mechanism are different; and
a recess to receive a protruding portion of an attached imaging component, wherein the recess:
comprises an opening for unattenuated transmission of x-ray beams generated by the attached imaging component through the support structure;
provides shielding around an inside of an edge of the opening to attenuate x-ray transmission through the edge of the opening;
wherein the protruding portion is a port extension of the attached imaging component; and
wherein the support structure is a rotary member configured to rotate about a patient.

8. The support structure of claim 7, further comprising:
a stationary structure, a top cap, or a collimator.

9. The support structure of claim 7, further comprising:
a base; and
a button that extends outward from the base at a height that is larger than a depth of the recess.

10. A gantry, comprising:
a support structure, comprising: an attachment mechanism to allow imaging components to be attached thereto; and a recess to receive a port extension of an attached imaging component; wherein the recess comprises an opening for unattenuated transmission of x-rays through the support structure from an imaging component and provides shielding around an inside edge of the opening of the recess to attenuate x-ray transmission through the inside edge of the opening of the recess; and
an imaging component attached to the support structure and that emits x-rays; the imaging component comprising the port extension that: (a) protrudes outwards from a side of the imaging component wherefrom the imaging component attaches to the support structure; (b) frames an opening from the imaging component to allow unattenuated x-rays to emit from the imaging component towards the support structure; and (c) provides shielding around an edge of an opening of the port extension to attenuate x-ray transmission through the edge of the opening of the port extension, wherein the port extension does not physically contact the support structure or the recess.

11. The gantry of claim 10, wherein:
the port extension protrudes into the recess such that the edge of the opening of the port extension provides a primary shielding effect upon scatter x-ray radiation and the inside edge of the opening of the recess provides a secondary shielding effect upon the scatter x-ray radiation.

12. The gantry of claim 10, wherein:
a depth of the recess is larger than a height of the port extension.

13. The gantry of claim 10, wherein:
a width of the recess is larger than a width of the port extension; and
a length of the recess is larger than a length of the port extension.

14. The gantry of claim 10, wherein:
the support structure comprises a stationary structure, a rotary member, a top cap, or a collimator.

15. The gantry of claim 10, further comprising:
a computed tomography system gantry or a diagnostic x-ray system gantry.

16. The gantry of claim 10, further comprising:
a detector assembly attached to the support structure for receiving x-rays and transmitting detected image data; and
an image reconstructor for receiving the transmitted detected image data and reconstructing images therefrom.

17. The gantry of claim 10, wherein:
the attachment mechanism comprises a primary attachment mechanism and a secondary attachment mechanism;
the imaging component can be attached to the support structure by the primary attachment mechanism; and the imaging component can be attached to the support structure by the secondary attachment mechanism, the secondary attachment mechanism being a T-slot interface.

18. The gantry of claim 10, wherein:
the opening of the port extension and the opening of the recess are substantially a same shape and size.

19. The gantry of claim 10, further comprising:
a button that extends outward from the support structure at a height that is larger than a depth of the recess; and
a pin extending outward from the imaging component in a same direction as the port extension, wherein a height of the pin is larger than a height of the port extension;
wherein the height of the button and the height of the pin are substantially the same.

20. A method of interfacing an x-ray tube with a support structure, comprising:
sliding the x-ray tube across a surface of the support structure;
wherein the x-ray tube comprises:
a port extension that protrudes outwards from a side of an imaging component, wherein the imaging component attaches to the support structure at the side; and
a pin extending outward from the imaging component in a same direction as the port extension, wherein a height of the pin is larger than a height of the port extension;
wherein the support structure comprises a button that extends outward from the support structure at a height that is larger than the height of the port extension; wherein the height of the button and the height of the pin are substantially the same; and
wherein, during sliding of the x-ray tube across the surface of the support structure, the pin and the button force separation between the x-ray tube and the support structure such that the port extension does not come into contact with the support structure.

* * * * *